(12) United States Patent
Ishii et al.

(10) Patent No.: US 6,815,559 B2
(45) Date of Patent: Nov. 9, 2004

(54) PROCESS FOR PRODUCING 3,3,3-TRIFLUORO-2-HYDROXYPROPIONIC ACID OR ITS DERIVATIVE

(75) Inventors: Akihiro Ishii, Saitama (JP); Masatomi Kanai, Saitama (JP); Yokusu Kuriyama, Saitama (JP); Manabu Yasumoto, Saitama (JP); Kenjin Inomiya, Saitama (JP)

(73) Assignee: Central Glass Company, Limited, Yamaguchi (JP)

( * ) Notice: Subject to any disclaimer, the term of this patent is extended or adjusted under 35 U.S.C. 154(b) by 0 days.

(21) Appl. No.: 10/464,838

(22) Filed: Jun. 19, 2003

(65) Prior Publication Data

US 2004/0049076 A1 Mar. 11, 2004

(30) Foreign Application Priority Data

Jun. 20, 2002 (JP) ........................................ 2002-179554

(51) Int. Cl.$^7$ .............................................. C07C 53/00
(52) U.S. Cl. ...................... 562/512; 560/179; 560/184; 562/512; 562/579; 562/586
(58) Field of Search ................................ 562/512, 579, 562/586; 560/179, 184

(56) References Cited

U.S. PATENT DOCUMENTS

| 4,052,460 A | * 10/1977 | Dickore et al. ............. 568/393 |
| 6,020,518 A | 2/2000 | Matsumoto et al. |
| 2002/0026081 A1 | 2/2002 | Onishi et al. |

FOREIGN PATENT DOCUMENTS

| DE | 2648300 | 7/1977 |
| EP | 1300391 | 4/2003 |
| JP | 3148249 | 6/1991 |
| JP | 5070406 | 3/1993 |
| JP | 5078277 | 3/1993 |
| JP | 5078278 | 3/1993 |
| JP | 10139724 | 5/1998 |
| JP | 10287609 | 10/1998 |
| JP | 10330308 | 12/1998 |
| JP | 11001451 | 1/1999 |
| JP | 2000063306 | * 2/2000 |
| JP | 2001226316 | 8/2001 |
| JP | 2002080429 | 3/2002 |
| WO | 98/07687 | 2/1998 |
| WO | 00/55113 | 9/2001 |
| WO | 02/00601 | 1/2002 |

OTHER PUBLICATIONS

Nippon Kagaku Kaishi, (1989) vol. 9, pp. 1576–1586.*
Toshimasa Katagiri, et al., "Synthesis of Trifluorolactic Acid from 1,2–Epoxy–3,3,3–Trifluoropropane.—One Pot Tandem Ring Opening–Oxidation Reaction of Epoxide–" Synlett, vol. 7, pp. 507–508, 1994.
C. Huennefeld, et al., "Ergiebige Herstellung von (R)– und (S)–3,3,3–Trifluormilchsaeure und von (R)– und (S)–(Trifluormethyl)oxiran" Chem. Ber., vol. 125, No. 12, pp. 2795–2802, 1992.
Nippon Kagaku Kaishi No. 9, pp. 1576–1586, 1989.
Yoshichika Kuroki, et al., Enantioselective Rhodium(I-)–Catalyzed Hydrogenation of Trifluoromethyl Ketones Organic Letters, vol. 3, No. 3, pp. 457–459, 2001.
Yoshichika Kuroki, et al., "Enantioslective synthesis of 1,1,1–trifluoroalkan–2–ols by ruthenium–catalzed hydrogenation" Tetrahedron Letters, vol. 41, pp. 4603–4607, 2000.
Nicholas J. Lawrence, et al., "An efficient protocol for the reduction of ketones with tin(II) complexes and PMHS" Tetrahedron Letters, vol. 41, pp. 4507–4512, 2000.
Huaxue Gongcheng (Xilan, China), 28(4) pp. 44.45, 2000.
A. Bandyopadhyay, et al., "A New Route for Synthesis of Aromatic –Keto Acid" J. Indian Chem. Soc. vol. 66, pp. 239–240, 1989.
Alberto Sala, et al., "Synthesis and Antibacterial Properties of 7–[2–(3–Substituted–5–Isoxazolyl)–2–Methoxyiminoacetamido]Cephalosporanic Acid Derivatives" The Journal of Antibiotics vol. 40, No. 11, pp. 1555–1562, 1987.
Peter Lugosi, et al., "Synthesis of 3–Haloisoxazoles by Novel Oxidative Degradation of the Side–Chain of 3.(3.Halo–Isoxazol–5–Yl) Propionic Acids" Tetrahedron Letters, vol. 37, No. 17, pp. 3061–3065, 1981.
Toshiyuki Tanaka, et al., "Synthesis of Lactic Acid from 1,1–Dichloroacetone" vol. 28, No. 7, pp. 501–502, 1979.

* cited by examiner

Primary Examiner—Rita Desai
Assistant Examiner—Hector M. Reyes
(74) Attorney, Agent, or Firm—Crowell & Moring LLP

(57) ABSTRACT

The invention relates to a process for producing 3,3,3-trifluoro-2-hydroxypropionic acid. This process includes the step of (a) bringing a 1,1-dihalogeno-3,3,3-trifluoroacetone into contact with a basic aqueous solution. The obtained 3,3,3-trifluoro-2-hydroxypropionic acid may be reacted with a $C_1$–$C_6$ lower alcohol under an acidic condition, thereby producing a 3,3,3-trifluoro-2-hydroxypropionate. This propionate may be reacted with a hydride reducing agent (e.g., sodium borohydride), thereby producing 3,3,3-trifluoro-2-hydroxypropanol. These products (i.e., 3,3,3-trifluoro-2-hydroxypropionic acid and its derivatives) are important intermediates for medicines and liquid crystals.

26 Claims, No Drawings

PROCESS FOR PRODUCING 3,3,3-TRIFLUORO-2-HYDROXYPROPIONIC ACID OR ITS DERIVATIVE

BACKGROUND OF THE INVENTION

The present invention relates to processes for producing 3,3,3-trifluoro-2-hydroxypropionic acid and its derivatives, which are useful intermediates for medicines and liquid crystals.

There are known the following first to fourth processes for producing 3,3,3-trifluoro-2-hydroxypropionic acid, which is represented by the formula 2.

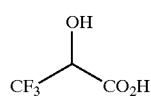

[2]

In the first process, it is derived from 3,3,3-trifluoro-2-hydroxypropanol or 3,3,3-trifluoropropene-1,2-oxide (see Synlett, 7, pp. 507–508 (1994); and Japanese Patent Application Publications 5-078277 and 5-078278).

In the second process, it is derived from trifluoropyruvate (see Chem. Ber., 125(12), pp. 2795–2802 (1992)).

In the third process, it is derived from trifluoroacetaldehyde (see Japanese Patent Application Publication 3-148249).

In the fourth process, it is derived from hexafluoroisopropanol (see Nippon Kagaku Kaishi No. 9, pp. 1576–1586 (1989)).

Other processes for producing 3,3,3-trifluoro-2-hydroxypropionic acid are disclosed in Japanese Patent Application Publications 2002-080429 and 2001-226316; Organic Letters, 3(3), pp. 457–459 (2001); Tetrahedron Letters, 41(23), pp. 4603–4607 (2000), and Tetrahedron Letters, 41(22), pp. 4507–4512 (2000).

Although it is possible to obtain 3,3,3-trifluoro-2-hydroxypropionic acid with a relatively high yield by the above conventional processes, the raw materials (i.e., trifluoromethyl-containing compounds) used in these processes have very high prices. Therefore, these processes are not suitable for industrially producing 3,3,3-trifluoro-2-hydroxypropionic acid.

The following reaction scheme is taught in WO 02/00601 corresponding to European Patent Application EP 1300391 A1; WO 00/55113 corresponding to U.S. Patent Application Publication 2002/0026081 A1; Huaxue Gongcheng (Xilan, China), 28(4), pp. 44–45, 51 (2000); Japanese Patent Application Publication 10-139724; WO 98/07687 corresponding to U.S. Pat. No. 6,020518; J. Indian Chem. Soc., 66(4), pp. 239–240 (1989); J. Antibiot., 40(11), pp. 1555–1562 (1987); Tetrahedron, 37(17), pp. 3061–3065 (1981); Yukagaku, 28(7), pp. 501–502 (1979); and German Patent Application Publication 2648300 corresponding to U.S. Pat. No. 4,052,460.

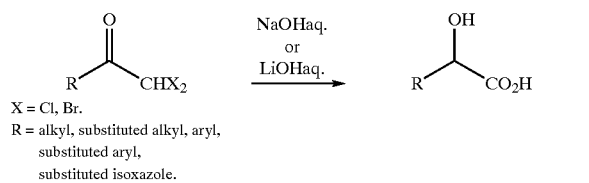

X = Cl, Br.
R = alkyl, substituted alkyl, aryl,
    substituted aryl,
    substituted isoxazole.

Furthermore, it is disclosed in Chem. Ber., 125(12), pp. 2795–2802 (1992) that 3,3,3-trifluoro-2-hydroxypropionic acid alkyl ester is protected at its hydroxyl group (bonded to the second carbon) with a THP (tetrahydropyranyl) group, and then its alkoxycarbonyl group (—COOR) is reduced to a hydroxymethyl group (—CH$_2$OH) using lithium aluminum hydride. Then, it is necessary to conduct a deprotection to produce 3,3,3-trifluoro-2-hydroxypropanol. Thus, the process of this publication is cumbersome for industrial production.

Japanese Patent Application Publication 2000-063306 discloses that 1,1-dichloro-3,3,3-trifluoroacetone is hydrolyzed in the presence of disodium hydrogenphosphate to trifluoropropanetetraol. It is further disclosed in this publication that the hydrolysis is conducted at a pH of from 2 to 9.

Japanese Patent Application Publication 5-70406 discloses a process for producing a β, β,β-trifluorolactic acid ester by reacting β,β,β-trifluorolactic acid with an alcohol (having a carbon atom number of at least 3) in the presence of a catalyst.

SUMMARY OF THE INVENTION

It is an object of the present invention to provide a process for efficiently producing 3,3,3-trifluoro-2-hydroxypropionic acid or its derivative(s), which are useful intermediates for medicines and liquid crystals.

According to the present invention, there is provided a process for producing 3,3,3-trifluoro-2-hydroxypropionic acid represented by the formula 2. This process includes the step of (a) bringing a 1,1-dihalogeno-3,3,3-trifluoroacetone represented by the formula 1 into contact with a basic aqueous solution (for example, having a pH of 12 or higher),

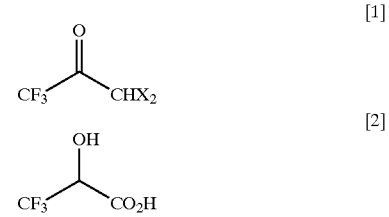

wherein X is Cl, Br or I.

The above raw material, 1,1-dihalogeno-3,3,3-trifluoroacetone, is industrially available with a low price.

It is possible to convert 3,3,3-trifluoro-2-hydroxypropionic acid into 3,3,3-trifluoro-2-hydroxypropanol represented by the formula 4 almost quantitatively, by a process including the steps of:

(b) reacting the 3,3,3-trifluoro-2-hydroxypropionic acid, which has been obtained by the above step (a), with a lower alcohol represented by the formula 5, under an acidic condition, thereby producing a 3,3,3-trifluoro-2-hydroxypropionate represented by the formula 3; and (c) reacting the 3,3,3-trifluoro-2-hydroxypropionate with a hydride reducing agent, thereby producing the 3,3,3-trifluoro-2-hydroxypropanol,

ROH [5]

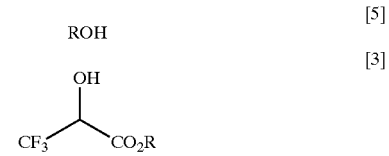

[3]

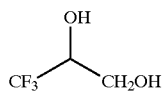

[4]

wherein R is a $C_1$–$C_6$ lower alkyl group.

It is possible by the above step (c) to efficiently reduce the alkoxycarbonyl group (—$CO_2R$) into the hydroxymethyl group (—$CH_2OH$) using a hydride reducing agent (e.g., sodium borohydride), without necessity of protecting the hydroxyl group (bonded to the second carbon) of the raw material, 3,3,3-trifluoro-2-hydroxypropionate and without necessity of the following deprotection. Thus, it is possible to easily obtain 3,3,3-trifluoro-2-hydroxypropanol with high yield and less load in industrial production.

The above-mentioned exemplary hydride reducing agent, sodium borohydride, is low in price and easy for handling. Thus, this sodium borohydride is considerably superior in safety and economy to lithium aluminum hydride.

DESCRIPTION OF THE PREFERRED EMBODIMENTS

In general, strongly basic condition (for example, having a pH of 12 or higher) has been considered as being not preferable for trifluoromethyl-containing compounds due to the tendency of decomposition of the trifluoromethyl group under such condition. The inventors, however, tried to bring the above 1,1-dihalogeno-3,3,3-trifluoroacetone into contact with a basic aqueous solution. With this, we unexpectedly found that the decomposition of the trifluoromethyl group does actually not occur and thereby the target product, 3,3,3-trifluoro-2-hydroxypropionic acid, can be obtained with high yield.

The above-mentioned steps (a), (b) and (c) for producing 3,3,3-trifluoro-2-hydroxypropanol can be shown by the following reaction scheme. As stated above, a target product of the present invention, 3,3,3-trifluoro-2-hydroxypropionic acid, can be obtained by the step (a).

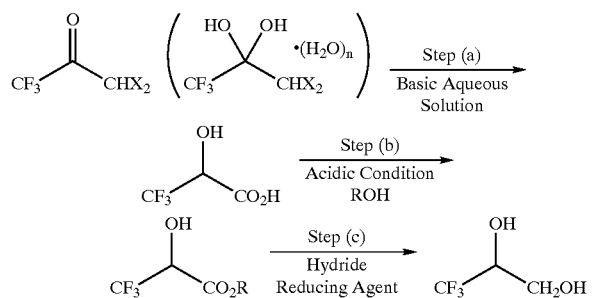

The step (a) is described in detail as follows. It is possible to efficiently produce 1,1-dichloro-3,3,3-trifluoroacetone, which can be the raw material of the step (a), by a process of Japanese Patent Application Publication 10-287609, 10-330308, 11-001451 or 2000-063306, in which pentachloroacetone is fluorinated in a gas or liquid phase into 1,1-dichloro-3,3,3-trifluoroacetone. Similarly, it is possible to obtain 1,1-dibromo-3,3,3-trifluoroacetone and 1,1-diiodo-3,3,3-trifluoroacetone by fluorinating pentabromoacetone and pentaiodoacetone, respectively.

Although the obtained 1,1-dihalogeno-3,3,3-trifluoroacetone itself can be used as the raw material of the step (a), it can be used in the step (a) as a hydrate since it mixes freely with water. This hydrate is easy for handling and can have, for example, the following formula 6:

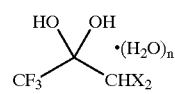

[6]

wherein X is defined as in the formula 1, and n is a number greater than 0. Furthermore, it is optional to mix 1,1-dihalogeno-3,3,3-trifluoroacetone with a solvent (e.g., alcohol) other than water to form a solvate. This solvate can also be used as the raw material of the step (a). Thus, 1,1-dihalogeno-3,3,3-trifluoroacetone of the formula 1 to be used in the step (a) is defined in the present specification as including its hydrate and solvate.

In case that 1,1-dihalogeno-3,3,3-trifluoroacetone is used as its hydrate in the step (a), the amount of water relative to that of 1,1-dihalogeno-3,3,3-trifluoroacetone for preparing the hydrate is not particularly limited. This water is in an amount of preferably 1–10 moles, more preferably 1–5 moles, relative to 1 mol of 1,1-dihalogeno-3,3,3-trifluoroacetone. A typical exemplary hydrate is a trihydrate in which 3 moles of water coexist with 1 mole of 1,1-dihalogeno-3,3,3-trifluoroacetone. This trihydrate is represented by the formula 6, in which n equals to 2. Using too much amount of water for preparing the hydrate is not problematic to the reactivity, but lowers the productivity. Therefore, it is not preferable.

The type of a base for preparing the basic aqueous solution of the step (a) is not particularly limited. It is preferably an inorganic base (e.g., sodium hydroxide, potassium hydroxide, lithium hydroxide, sodium carbonate, and potassium carbonate), in terms of reactivity and of preventing the production of impurities that are difficult to be separated from the target product. It is optional to combine a plurality of inorganic bases for preparing the basic aqueous solution. Of the above examples, sodium hydroxide and potassium hydroxide are preferable, since they are high in basicity and since pH of the resulting basic aqueous solution can easily be controlled. In particular, sodium hydroxide is more preferable.

In the step (a), the base concentration of the basic aqueous solution is not particularly limited and can suitably be set in view of solubility of the inorganic base in water. The base concentration is preferably 1–50 wt %, more preferably 1–40 wt %, of the basic aqueous solution.

The base of the basic aqueous solution may be in an amount of at least 2 equivalents, preferably 2–20 equivalents, more preferably 2–10 equivalents, relative to 1 equivalent of the compound of the formula 1.

The pH of the basic aqueous solution during the step (a) is preferably 12 or higher, more preferably 12–14, still more preferably 13–14. Although it may have a pH within these ranges by using the base in the above-described amount, it is preferable to measure pH of the reaction mixture at a suitable interval by using a known measure (e.g., pH test paper). In fact, pH of the reaction mixture (solution) gradually lowers as the reaction of the step (a) proceeds, since a halogenated hydracid (e.g., hydrochloric acid) is generated by the reaction. If the pH becomes too low, conversion and selectivity of the reaction become extremely low. Therefore, it is preferable in the reaction of the step (a) to measure pH of the reaction mixture at a suitable interval and to add the base to the reaction mixture when the measured pH is lower than 12.

It is optional to use a reaction solvent in the step (a). Its nonlimitative examples include (1) aliphatic hydrocarbons such as n-pentane, n-hexane, cyclohexane, and n-heptane; (2) aromatic hydrocarbons such as benzene, toluene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and dioxane; (5) esters such as ethyl acetate and n-butyl acetate; (6) nitriles such as acetonitrile and propionitrile; (7) alcohols such as methanol, ethanol, n-propanol, and i-propanol; and (8) water. Of these, preferable examples are diethyl ether, tetrahydrofuran, t-butyl methyl ether, methanol, ethanol, i-propanol, and water. In particular, tetrahydrofuran, methanol, ethanol, and water are more preferable. It is possible to use a single solvent or a mixture of at least two of these. It is possible to conduct the reaction without using any reaction solvent.

The reaction temperature of the step (a) may be from $-10°$ C. to $+100°$ C., preferably $-10°$ C. to $+80°$ C., more preferably $0°$ C. to $+60°$ C.

The way of adding the substrate is not particularly limited in the step (a). It is, however, preferable to add the substrate gradually in order to stably maintain the temperature of the reaction mixture, since the reaction of the step (a) generates a relatively strong heat. For example, the compound of the formula 1 may be added dropwise to the basic aqueous solution, or the basic aqueous solution may be added dropwise to the compound of the formula 1. In this case, the dropping rate may suitably be adjusted such that the inside temperature of the reactor does not become significantly higher than the outside set temperature. For example, it may be adjusted that the temperature difference between the inside and the outside is $10°$ C. or less.

In the reaction of the step (a), it is optional to stir the reaction mixture for about 1–3 hrs for ageing, after gradually adding the substrate. A stirring for a very long time (e.g., 24 hr or longer) may not further improve yield. Such stirring may lower the efficiency of the reaction and thus may not be preferable.

Post-treatment of the step (a) is not particularly limited. At the end of the reaction of the step (a), the target product, 3,3,3-trifluoro-2-hydroxypropionic acid represented by the formula 2, is present as a salt formed by a reaction of 3,3,3-trifluoro-2-hydroxypropionic acid with the base in an excessive amount. Thus, it is easily possible to add an inorganic acid to a reaction liquid obtained by the step (a) to convert this salt into 3,3,3-trifluoro-2-hydroxypropionic acid, followed by extraction with an organic solvent to isolate 3,3,3-trifluoro-2-hydroxypropionic acid. The inorganic acid may be selected from hydrochloric acid, hydrobromic acid, sulfuric acid, and phosphoric acid. Of these, hydrochloric acid and sulfuric acid are preferable, and hydrochloric acid is more preferable.

The above-mentioned extraction solvent may be selected from (1) aliphatic hydrocarbons such as n-pentane, n-hexane, cyclohexane, and n-heptane; (2) aromatic hydrocarbons such as benzene, toluene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and dioxane; and (5) esters such as ethyl acetate and n-butyl acetate. Of these, preferable examples are toluene, t-butyl methyl ether, and ethyl acetate. In particular, t-butyl methyl ether and ethyl acetate are more preferable. It is possible to use a single solvent or a mixture of at least two of these.

In the step (a), the resulting extracted solution may be subjected to washing with water and brine, drying, and concentration, thereby obtaining a crude product. According to need, the crude product may be subjected to purification (e.g., the use of activated carbon, rectification, recrystallization, and column chromatography), thereby obtaining 3,3,3-trifluoro-2-hydroxypropionic acid of the formula 2 with high purity.

The step (b) is described in detail as follows. The step (b) can be conducted by reacting 3,3,3-trifluoro-2-hydroxypropionic acid, which has been obtained by the step (a), with a lower alcohol represented by the formula 5, in the presence of an acid catalyst, thereby producing 3,3,3-trifluoro-2-hydroxypropionate represented by the formula 3. The step (b) may be conducted in accordance with a conventional esterification.

The lower alcohol represented by the formula 5 may be selected from methanol, ethanol, n-propanol, n-butanol, n-pentanol, n-hexanol, i-propanol, 2-butanol, and cyclohexanol.

The lower alcohol of the formula 5 may be in an amount of 1 equivalent or greater, relative to 1 equivalent of 3,3,3-trifluoro-2-hydroxypropionic acid. In particular, it is possible to use an excessive amount of the lower alcohol as a reaction solvent.

The acid catalyst for conducting the step (b) may be selected from organic acids (e.g., benzenesulfonic acid, p-toluenesulfonic acid, 10-camphorsulfonic acid) and inorganic acids (e.g., hydrochloric acid, hydrobromic acid, sulfuric acid, phosphoric acid, zinc chloride, and titanium tetrachloride). Of these, p-toluenesulfonic acid and sulfuric acid are preferable. In particular, sulfuric acid is more preferable.

The acid catalyst may be in a catalytic amount relative to that of 3,3,3-trifluoro-2-hydroxypropionic acid. It is preferably 0.001–1 equivalent, more preferably 0.005–0.5 equivalents, relative to one equivalent of 3,3,3-trifluoro-2-hydroxypropionic acid.

In the step (b), water is produced as a by-product as the reaction proceeds. It is possible to accelerate the reaction by removing such water from the reaction system. Thus, the reaction of the step (b) can be conducted in the presence of a dehydrating agent such as zeolite (e.g., molecular sieve), phosphorus pentoxide, anhydrous sodium sulfate, and anhydrous magnesium sulfate, to remove water during the step (b). In case that the lower alcohol of the formula 5 is immiscible with water, has a specific gravity less than that of water, and forms an azeotropic mixture with water, it is possible to remove water from a Dean-Stark trap, while the reaction is conducted under reflux with or without reaction solvent (e.g., benzene and toluene).

The reaction temperature of the step (b) may be from $0°$ C. to $+200°$ C., preferably from $0°$ C. to $+150°$ C., more preferably from $0°$ C. to $+100°$ C. The reaction time for conducting the step (b) may be 48 hr or shorter and may vary depending on the reaction conditions. Therefore, it is preferable to terminate the reaction after confirming that the raw material was almost completely consumed, by checking the progress of the reaction by a suitable analytical technique (e.g., gas chromatography, thin layer chromatography, and NMR).

Post-treatment of the step (b) is not particularly limited. It is possible to easily obtain a crude product by subjecting a reaction mixture itself at the end of the reaction to distillation. This crude product can be used in the subsequent step (c). Alternatively, according to need, the crude product may be subjected to purification (e.g., the use of activated carbon, rectification, recrystallization, and column chromatography), thereby obtaining 3,3,3-trifluoro-2-hydroxypropionate of the formula 3 with very high purity.

The step (c) is described in detail as follows. As stated above, the step (c) can be conducted by reacting 3,3,3-trifluoro-2-hydroxypropionate of the formula 3 with a hydride reducing agent, thereby producing 3,3,3-trifluoro-2-hydroxypropanol of the formula 4.

The hydride reducing agent may be selected from (1) aluminum hydrides such as (i-Bu)$_2$AlH, (i-Bu)$_3$Al, [2,6-(t-

Bu)$_2$-4-MePh]Al(i-Bu)$_2$, LiAlH$_4$, LiAlH(OMe)$_3$, LiAlH(O-t-Bu)$_3$ and NaAlH$_2$(OCH$_2$CH$_2$OCH$_3$)$_2$; (2) boron hydrides such as diborane, BH$_3$-THF, BH$_3$—SMe$_2$, BH$_3$—NMe$_3$, 9-BBN, NaBH$_4$, NaBH$_4$—CeCl$_3$, LiBH$_4$, Zn(BH$_4$)$_2$, Ca(BH$_4$)$_2$, Li(n-Bu)BH$_3$, NaBH(OMe)$_3$, NaBH(OAc)3, NaBH$_3$CN, Et$_4$NBH$_4$, Me$_4$NBH(OAc)$_3$, (n-Bu)$_4$NBH$_3$CN, (n-Bu)$_4$NBH(OAc)$_3$, Li(sec-Bu)$_3$BH, K(sec-Bu)$_3$BH, LiSia$_3$BH, KSia$_3$BH, LiEt$_3$BH, KPh$_3$BH, (Ph$_3$P)$_2$CuBH$_4$, ThxBH$_2$, Sia$_2$BH, catechol borane, IpcBH$_2$ and Ipc$_2$BH; and (3) silicon hydrides such as Et$_3$SiH, PhMe$_2$SiH, Ph$_2$SiH$_2$ and PhSiH$_3$—Mo(CO)$_6$, where Bu represents butyl group, Ph represents phenyl group, Me represents methyl group, THF represents tetrahydrofuran, 9-BBN represents 9-borabicyclo[3,3,1]nonane, Ac represents acetyl group, Sia represents siamyl group, Et represents ethyl group, Thx represents thexyl group, and Ipc represents isopinocampheyl group. Among these, LiAlH$_4$, diborane, NaBH$_4$ and LiBH$_4$ are preferable. NaBH$_4$ is particularly more preferable, since it is low in price and can easily be used in a large amount. These hydride reducing agents can also be used in the presence of various inorganic salts.

The hydride reducing agent may be in an amount of 0.25 equivalents or greater, preferably 0.25–10 equivalents, more preferably 0.25–7.0 equivalents, relative to one equivalent of 3,3,3-trifluoro-2-hydroxypropionate.

It is preferable to conduct the reaction of the step (c) in solvent. Its nonlimitative examples include (1) aliphatic hydrocarbons such as n-pentane, n-hexane, cyclohexane, and n-heptane; (2) aromatic hydrocarbons such as benzene, toluene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and dioxane; (5) esters such as ethyl acetate and n-butyl acetate; (6) nitriles such as acetonitrile and propionitrile; (7) alcohols such as methanol, ethanol, n-propanol, and i-propanol; and (8) carboxylic acids such as acetic acid, propionic acid, and butyric acid. Of these, preferable examples are diethyl ether, tetrahydrofuran, t-butyl methyl ether, methanol, ethanol, and i-propanol. In particular, tetrahydrofuran, methanol, ethanol, and i-propanol are more preferable. It is possible to use a single solvent or a mixture of at least two of these.

The reaction temperature of the step (c) may be from −100° C. to +100° C., preferably −80° C. to +80° C., more preferably −60° C. to +60° C. The reaction time for conducting the step (c) may be 24 hr or shorter and may vary depending on the reaction conditions. Therefore, it is preferable to terminate the reaction after confirming that the raw material was almost completely consumed, by checking the progress of the reaction by a suitable analytical technique (e.g., gas chromatography, thin layer chromatography, and NMR).

In a reaction mixture at the end of the reaction of the step (c), 3,3,3-trifluoro-2-hydroxypropanol of the formula 4 is stably present as a five-membered cyclic compound represented by the formula 7.

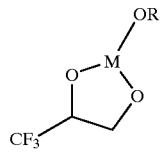

M = B, Al or Si
R = H, alkyl, CF$_3$CH(OH)CH$_2$ or CF$_3$CHCH$_2$OH

Thus, the target product is still mostly in the form of the above five-membered cyclic compound, even if the reaction mixture obtained by the step (c) is extracted with organic solvent.

It is, however, possible to easily hydrolyze the five-membered cyclic compound by treating the same with an inorganic acid (e.g., hydrochloric acid, hydrobromic acid, sulfuric acid, and phosphorus acid) or fluoride ions, thereby isolate 3,3,3-trifluoro-2-hydroxypropanol. In fact, it is possible to add an inorganic acid to a reaction product (containing the five-membered cyclic compound) of the step (c), followed by heating at a constant temperature, thereby isolating the target product (i.e., 3,3,3-trifluoro-2-hydroxypropanol) with high yield. Although the way of this isolation is not particularly limited, it can effectively be conducted by dissolving the reaction product of the step (c) in methanol, then by adding a sulfuric acid aqueous solution, and then by heating under reflux.

It is possible to conduct a solvent extraction with an organic solvent to collect 3,3,3-trifluoro-2-hydroxypropanol, which has been isolated by the above-mentioned acid treatment. Examples of the organic extraction solvent include (1) aliphatic hydrocarbons such as n-pentane, n-hexane, cyclohexane, and n-heptane; (2) aromatic hydrocarbons such as benzene, toluene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and dioxane; and (5) esters such as ethyl acetate and n-butyl acetate. Of these, preferable examples are toluene, diethyl ether, t-butyl methyl ether, and ethyl acetate. In particular, diethyl ether and ethyl acetate are more preferable. It is possible to use a single solvent or a mixture of at least two of these.

In the step (c), the resulting extracted solution may be subjected to washing with water and brine, drying, and concentration, thereby obtaining a crude product. According to need, the crude product may be subjected to purification (e.g., the use of activated carbon, rectification, recrystallization, and column chromatography), thereby obtaining 3,3,3-trifluoro-2-hydroxypropanol with high purity.

The following nonlimitative Examples are illustrative of the present invention.

EXAMPLE 1

The step (a) of the present invention was conducted as follows. At first, 235 g (1 mol, 1 eq.) of 1,1-dichloro-3,3,3-trifluoroacetone trihydrate were added dropwise by spending 2.5 hr to 533 g (4 mol, 4 eq.) of 30 wt % sodium hydroxide aqueous solution under cooling with ice, while the internal temperature of the reaction liquid was maintained at 25° C. or lower, followed by stirring for 1 hr. After that, 197 g (2 mol, 2 eq.) of 37 wt % hydrochloric acid aqueous solution were added dropwise to the reaction liquid under cooling with ice, while the internal temperature of the reaction liquid was maintained at 25° C. or lower. Then, 180 ml of water were added under room temperature to dissolve the precipitated sodium chloride. The resulting solution was extracted two times with 500 ml of ethyl acetate. Then, the combined organic layer was washed one time with 500 ml of saturated brine, concentrated and dried under vacuum, thereby obtaining 163 g of a crude product of 3,3,3-trifluoro-2-hydroxypropionic acid. This crude product was found by $^1$H-NMR to contain 81.5 wt % of 3,3,3-trifluoro-2-hydroxypropionic acid (yield: 92%). This crude product was used in the following step (b) of Example 2 without conducting a further purification. The obtained 3,3,3-trifluoro-2-hydroxypropionic acid was found to have the following characteristics.

$^1$H-NMR (standard substance: TMS; solvent: CD$_3$OD), δ ppm: 4.53 (q, 7.6 Hz, 1H);

$^{19}$F-NMR (standard substance: C$_6$F$_6$, solvent: CD$_3$OD), δ ppm: 87.75 (d, 7.6 Hz).

EXAMPLE 2

The step (b) of the present invention was conducted as follows. At first, 2.84 g of the crude product obtained by Example 1 (containing 16.07 mmol (1.00 eq.) of 3,3,3-trifluoro-2-hydroxypropionic acid) and 19.6 mg (0.20 mmol, 0.01 eq.) of 98% sulfuric acid were added to 20 ml of ethanol, followed by stirring for 43 hr with heating under reflux. The resulting reaction liquid itself was subjected to a vacuum distillation (52° C./3,500 Pa), thereby obtaining 1.87 g of white, needle-like crystals of ethyl 3,3,3-trifluoro-2-hydroxypropionate of the following formula 8. The yield was 68%. The obtained crude product (the white, needle-like crystals) was used in the following step (c) of Example 3 without conducting a further purification.

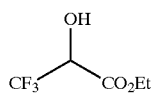

[8]

Ethyl 3,3,3-trifluoro-2-hydroxypropionate was found to have the following characteristics.

$^1$H-NMR (standard substance: TMS; solvent: CDCl$_3$), δ ppm: 1.35 (t, 7.6 Hz, 3H), 3.42 (br, 1H), 4.30–4.47 (m, 2H), 4.47 (q, 7.6 Hz, 1H);

$^{19}$F-NMR (standard substance: C$_6$F$_6$, solvent: CDCl$_3$), δ ppm: 85.58 (d, 7.6 Hz).

EXAMPLE 3

The step (c) of the present invention was conducted as follows. At first, 1.87 g (10.87 mmol, 1.00 eq.) of the white, needle-like crystals of ethyl 3,3,3-trifluoro-2-hydroxypropionate, which had been produced in Example 2, were dissolved in 20 ml of ethanol. Then, 0.41 g (10.84 mmol, 1.00 eq.) of sodium borohydride were added under cooling with ice, followed by stirring at room temperature for 12 hr. Then, the reaction was terminated by adding 10 ml of 10 wt % hydrochloric acid aqueous solution, followed by adding 5 ml of water to dissolve undissolved substances. The resulting liquid was extracted two times with 20 ml of diethyl ether. The combined organic layer was washed one time with 10 ml of saturated brine. The resulting organic layer was dried with anhydrous sodium sulfate, concentrated and dried under vacuum, thereby obtaining an organic matter residue. This organic matter residue was found by $^1$H-NMR to be formed mostly of a five-membered cyclic compound (represented by the following formula 9), obtained by a reaction of 3,3,3-trifluoro-2-hydroxypropanol with boron.

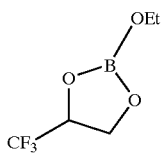

[9]

Then, to the total amount of the obtained organic matter residue 10 ml of methanol and 10 ml of 10 wt % sulfuric acid aqueous solution were added, followed by stirring for 24 hr with heating under reflux. After the reaction, methanol was distilled away, and the organic matter residue was dissolved by adding 20 ml of water. The obtained solution was extracted two times with 20 ml of diethyl ether. The combined organic layer was dried with anhydrous sodium sulfate, concentrated, dried under vacuum, and distilled under vacuum (62° C./1000 Pa), thereby obtaining 1.12 g of 3,3,3-trifluoro-2-hydroxypropanol as a purified distillate. The yield was 79%. The obtained 3,3,3-trifluoro-2-hydroxypropanol was found to have the following characteristics.

$^1$H-NMR (standard substance: TMS; solvent: CDCl$_3$), δ ppm: 2.02 (br, 1H), 3.06 (br, 1H), 3.83–3.92 (m, 2H), 4.03–4.13 (m, 1H);

$^{19}$F-NMR (standard substance: C$_6$F$_6$, solvent: CDCl$_3$), δ ppm: 84.05 (d, 7.6 Hz).

The entire contents of Japanese Patent Application No. 2002-179554 (filed Jun. 20, 2002), which is a basic Japanese application of the present application, are incorporated herein by reference.

What is claimed is:

1. A process for producing 3,3,3-trifluoro-2-hydroxypropionic acid represented by the formula 2, the process comprising the step of (a) bringing a 1,1-dihalogeno-3,3,3-trifluoroacetone represented by the formula 1 into contact with a basic aqueous solution,

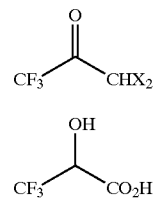

[1]

[2]

wherein X is Cl, Br or I.

2. A process according to claim 1, wherein the basic aqueous solution has a pH higher than 12.

3. A process according to claim 1, wherein the basic aqueous solution has a pH of from 12 to 14.

4. A process according to claim 1, wherein the basic aqueous solution has a pH of from 13 to 14.

5. A process according to claim 1, wherein, when pH of the basic aqueous solution becomes lower than 12 during the step (a), a base is added to the basic aqueous solution such that the basic aqueous solution has a pH higher than 12.

6. A process according to claim 1, wherein the basic aqueous solution comprises an inorganic base selected from the group consisting of sodium hydroxide, potassium hydroxide, lithium hydroxide, sodium carbonate, potassium carbonate, and mixtures of these.

7. A process according to claim 6, wherein the inorganic base is selected from the group consisting of sodium hydroxide, potassium hydroxide, and mixtures of these.

8. A process according to claim 7, wherein the inorganic base is sodium hydroxide.

9. A process according to claim 1, wherein the basic aqueous solution comprises 1–50 wt % of an inorganic base.

10. A process according to claim 1, wherein the basic aqueous solution comprises 1–40 wt % of an inorganic base.

11. A process according to claim 1, wherein the basic aqueous solution comprises a base in an amount of at least 2 equivalents, relative to one equivalent of the 1,1-dihalogeno-3,3,3-trifluoroacetone.

12. A process according to claim 1, wherein the basic aqueous solution comprises a base in an amount of from 2 to 20 equivalents, relative to one equivalent of the 1,1-dihalogeno-3,3,3-trifluoroacetone.

13. A process according to claim 1, wherein the basic aqueous solution comprises a base in an amount of from 2 to 10 equivalents, relative to one equivalent of the 1,1-dihalogeno-3,3,3-trifluoroacetone.

14. A process according to claim 1, wherein the step (a) is conducted at a temperature of from −10° C. to +100° C.

15. A process according to claim 1, wherein the step (a) is conducted at a temperature of from −10° C. to +80° C.

16. A process according to claim 1, wherein the step (a) is conducted at a temperature of from 0° C. to +60° C.

17. A process according to claim 1, wherein the step (a) is conducted at about room temperature or lower by cooling a reaction liquid of the step (a).

18. A process according to claim 1, wherein the step (a) is conducted by adding the 1,1-dihalogeno-3,3,3-trifluoroacetone dropwise to the basic aqueous solution.

19. A process according to claim 1, wherein the step (a) is conducted by adding the basic aqueous solution dropwise to the 1,1-dihalogeno-3,3,3-trifluoroacetone.

20. A process according to claim 1, further comprising the steps of:
(b) adding an inorganic acid to a reaction liquid obtained by the step (a) to convert a salt of the 3,3,3-trifluoro-2-hydroxypropionic acid into the 3,3,3-trifluoro-2-hydroxypropionic acid; and
(c) extracting a product of the step (b) with an organic solvent to isolate the 3,3,3-trifluoro-2-hydroxypropionic acid.

21. A process according to claim 20, wherein the inorganic acid of the step (b) is hydrochloric acid.

22. A process according to claim 20, wherein the organic solvent of the step (c) is selected from the group consisting of toluene, t-butyl methyl ether, ethyl acetate, and mixtures of these.

23. A process for producing 3,3,3-trifluoro-2-hydroxypropanol represented by the formula 4, the process comprising reacting a 3,3,3-trifluoro-2-hydroxypropionate, represented by the formula 3, with a hydride reducing agent,

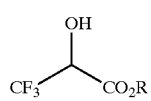   [3]

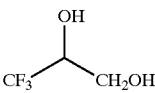   [4]

wherein R is a $C_1$–$C_6$ lower alkyl group.

24. A process according to claim 23, wherein the hydride reducing agent comprises sodium borohydride.

25. A process for producing 3,3,3-trifluoro-2-hydroxypropanol represented by the formula 4, the process comprising the steps of:
(a) reacting 3,3,3-trifluoro-2-hydroxypropionic acid represented by the formula 2, with a lower alcohol represented by the formula 5, under an acidic condition, thereby producing a 3,3,3-trifluoro-2-hydroxypropionate represented by the formula 3; and
(b) reacting the 3,3,3-trifluoro-2-hydroxypropionate with a hydride reducing agent, thereby producing the 3,3,3-trifluoro-2-hydroxypropanol,

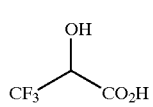   [2]

ROH   [5]

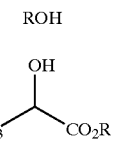   [3]

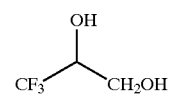   [4]

wherein R is a $C_1$–$C_6$ lower alkyl group.

26. A process for producing 3,3,3-trifluoro-2-hydroxypropanol represented by the formula 4, the process comprising the steps of:

(a) bringing a 1,1-dihalogeno-3,3,3-trifluoroacetone represented by the formula 1 into contact with a basic aqueous solution, thereby producing 3,3,3-trifluoro-2-hydroxypropionic acid represented by the formula 2;

(b) reacting the 3,3,3-trifluoro-2-hydroxypropionic acid with a lower alcohol represented by the formula 5, under an acidic condition, thereby producing a 3,3,3-trifluoro-2-hydroxypropionate represented by the formula 3; and (c) reacting the 3,3,3-trifluoro-2-hydroxypropionate with a hydride reducing agent, thereby producing the 3,3,3-trifluoro-2-hydroxypropanol,

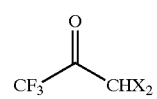   [1]

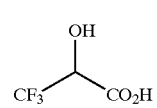   [2]

ROH   [5]

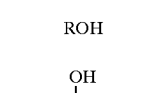   [3]

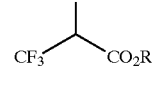   [4]

wherein X is Cl, Br or I; and R is a $C_1$–$C_6$ lower alkyl group.

* * * * *